(12) United States Patent
Sleeman et al.

(10) Patent No.: US 7,052,691 B2
(45) Date of Patent: May 30, 2006

(54) METHODS OF TREATING DIABETES BY BLOCKING VEGF-MEDIATED ACTIVITY

(75) Inventors: Mark W. Sleeman, Mahopac, NY (US); Stanley J. Wiegand, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 53 days.

(21) Appl. No.: 10/811,170

(22) Filed: Mar. 26, 2004

(65) Prior Publication Data

US 2004/0213787 A1 Oct. 28, 2004

Related U.S. Application Data

(60) Provisional application No. 60/458,790, filed on Mar. 28, 2003.

(51) Int. Cl.
- *A61K 38/18* (2006.01)
- *C07K 14/71* (2006.01)
- *C12N 15/62* (2006.01)

(52) U.S. Cl. .............. 424/134.1; 424/192.1; 514/2; 514/12; 530/350; 530/387.3; 536/23.4

(58) Field of Classification Search ............ None
See application file for complete search history.

(56) References Cited

U.S. PATENT DOCUMENTS 6,524,583 B1 * 2/2003 Thorpe et al. ........... 424/145.1
2003/0017977 A1    1/2003 Xia et al.

FOREIGN PATENT DOCUMENTS

| WO | WO 02/060489 A | 8/2000 |
|----|----------------|--------|
| WO | WO 00/75319 A  | 12/2000 |

OTHER PUBLICATIONS

Pettit et al. (1998). The development of site-specific drug-delivery systems for protein and peptide biopharmaceuticals. Trends Biotechnol 16: 343-349.*

De Vriese, A., et al., 2001, "Antibodies Against Vascular Endothelial Growth Factor Improve Early Renal Dysfunction in Experiment Diabetes", J. Am. Soc. Nephrol. 12:993-1000.

Ereemina, V., et al., 2003, "Glomerular-Specific Alterations of VEGF-A Expression Lead to Distinct Congenital and Acquired Renal Diseases", J. Clin. Invest. 111:707-716.

Cooper, M., et al., 1999, "Increased Renal Expression of Vascular Endothelial Growth Factor (VEGF) and Its Receptor VEGFR-2 in Experimental Diabetes", Diabetes, 48:2229-2239.

Flyvbjerg, A., et al., 2002, "Amelioration of Long-Term Renal Changes in Obese Type 2 Diabetic Mice by a Neutralizing Vascular Endothelial Growth Factor Antibody", Diabetes, 51:3090-3094.

Holash, J., et al., (2002) PNAS, 99(17):11393-11398.

Heidaran, M.A., et al., (1990) J. Biol. Chem. 265(31):18741-18744.

Cunningham, S.A., et al., (1997) Biochem. Biophys. Res. Comm. 231;596-599.

Fuh, G., et al., (1998) J. Biol. Chem. 273(18):11197-11204.

Wiesmann, C., et al., (1997) Cell, 91:695-704.

Barleon, B., et al., (1997) J. Biol. Chem. 272(16):10382-10388.

Davis-Smyth, T., et al., (1998) J. Biol. Chem. 273(6):3216-3222.

* cited by examiner

*Primary Examiner*—Brenda Brumback
*Assistant Examiner*—Jon M Lockard
(74) *Attorney, Agent, or Firm*—Valeta Gregg, Esq.

(57) ABSTRACT

Methods of treating diabetes in mammals, particularly humans, by blocking or inhibiting VEGF-mediated activity. A preferred inhibitor of VEGF-mediated activity is a VEGF antagonist such as a VEGF trap capable of binding and blocking VEGF.

13 Claims, 7 Drawing Sheets

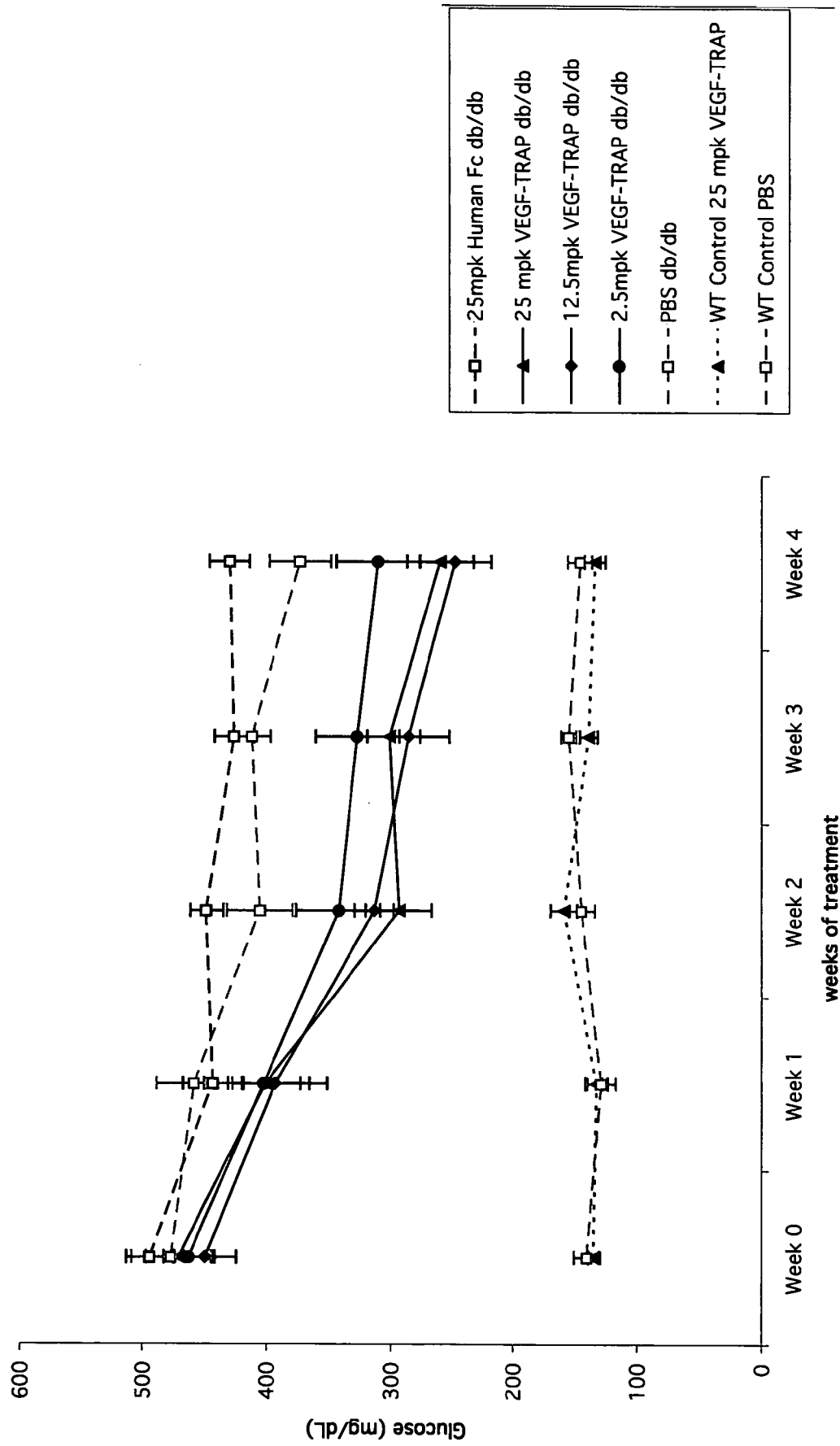

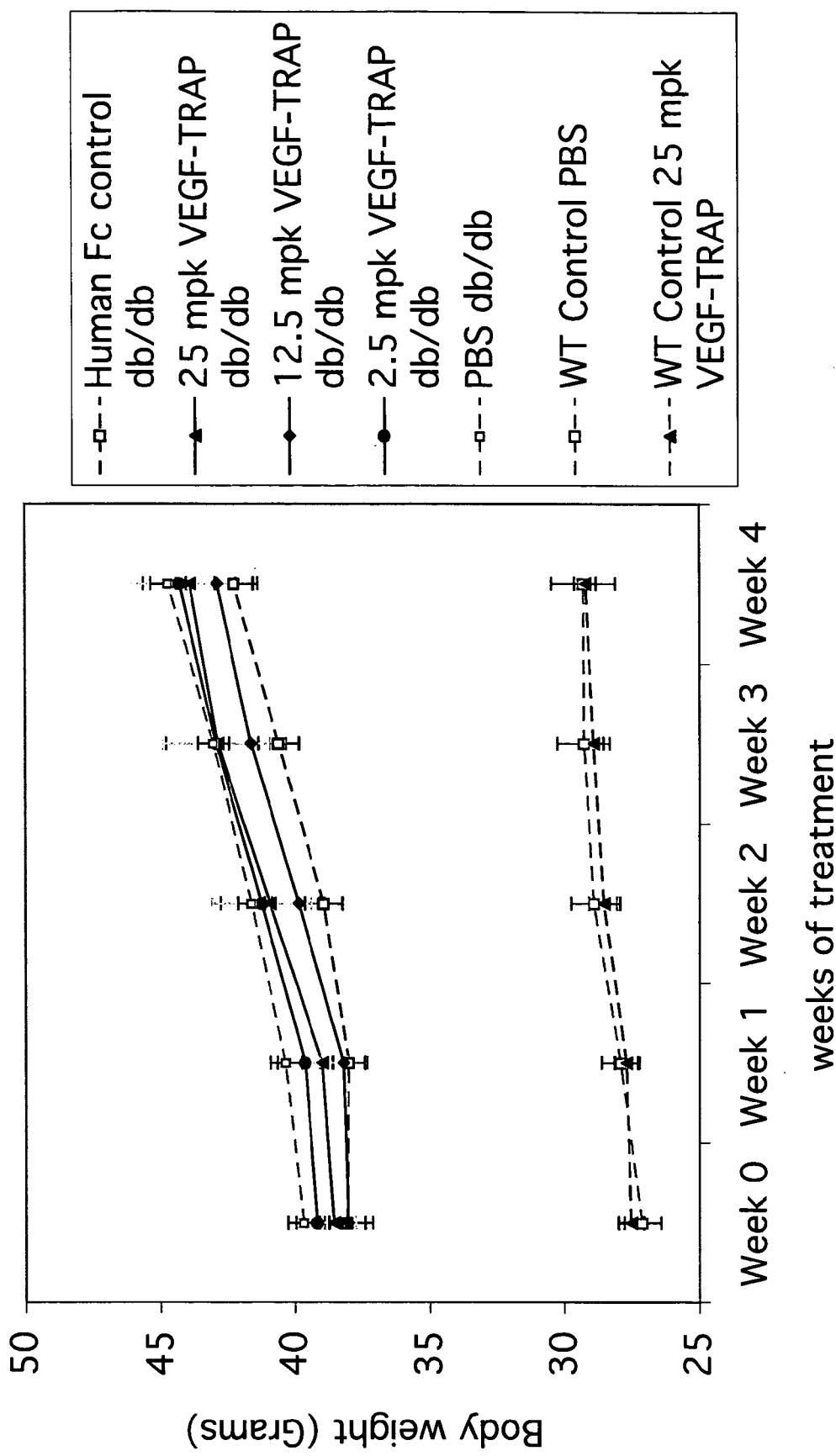
Fig 1B Body Weight

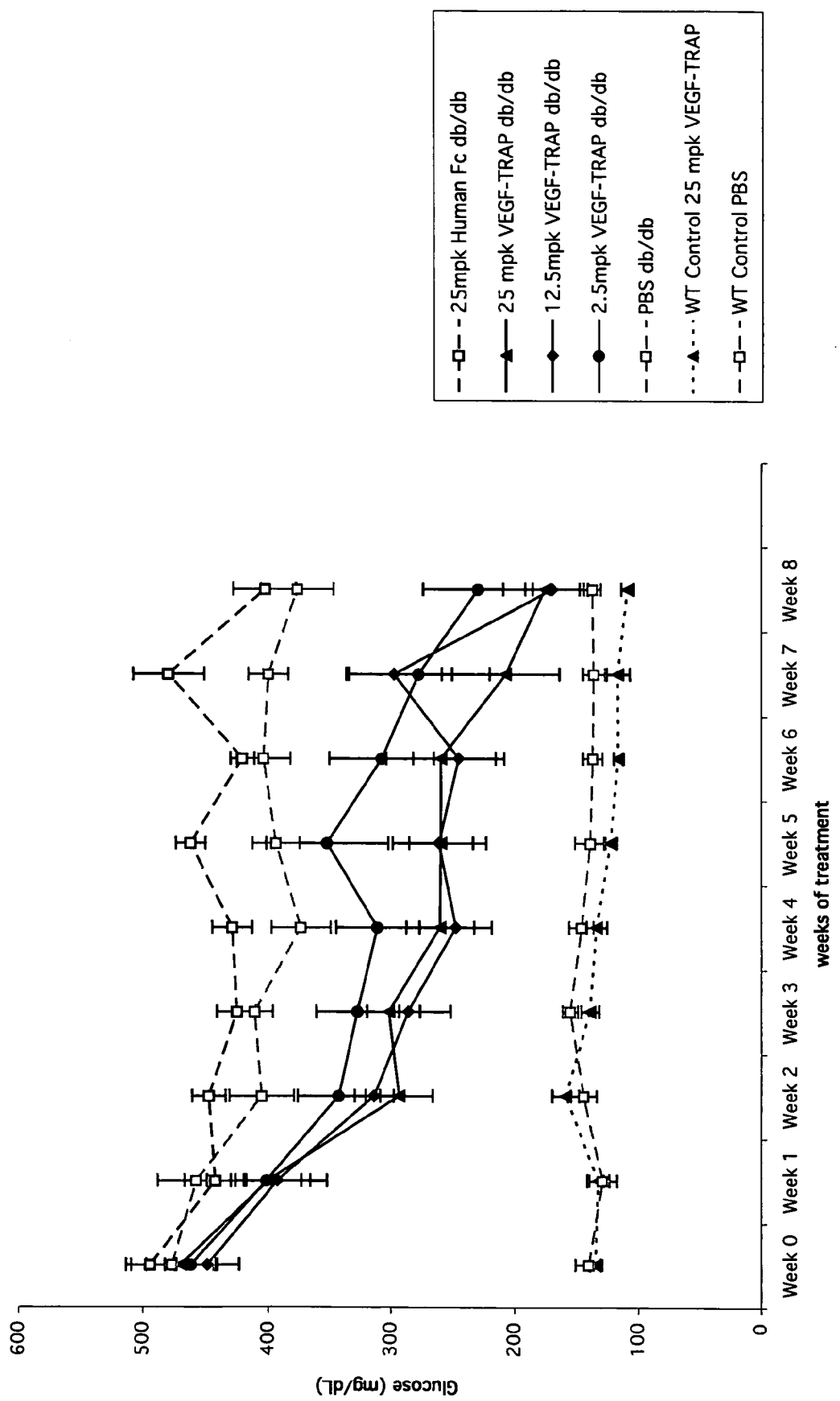

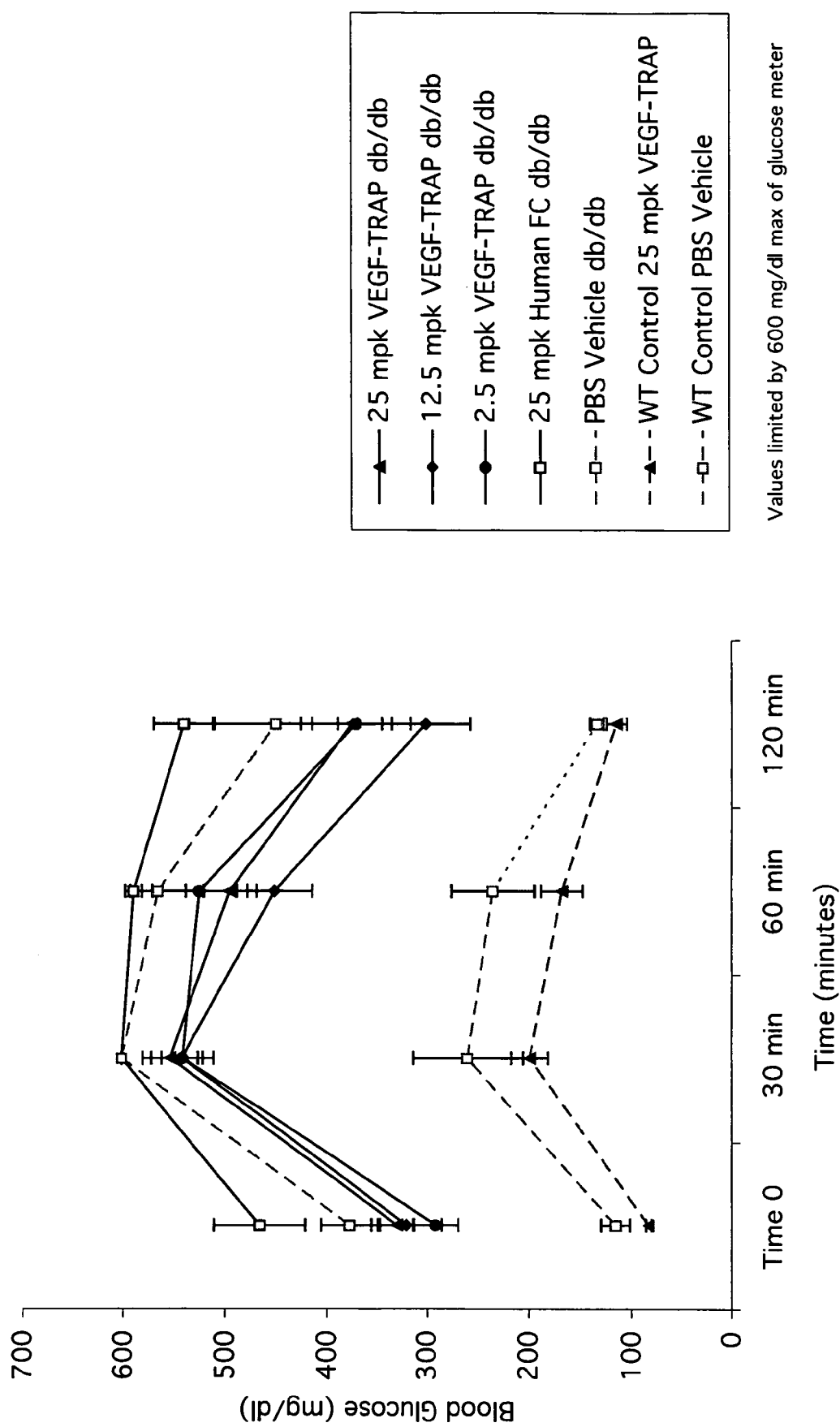

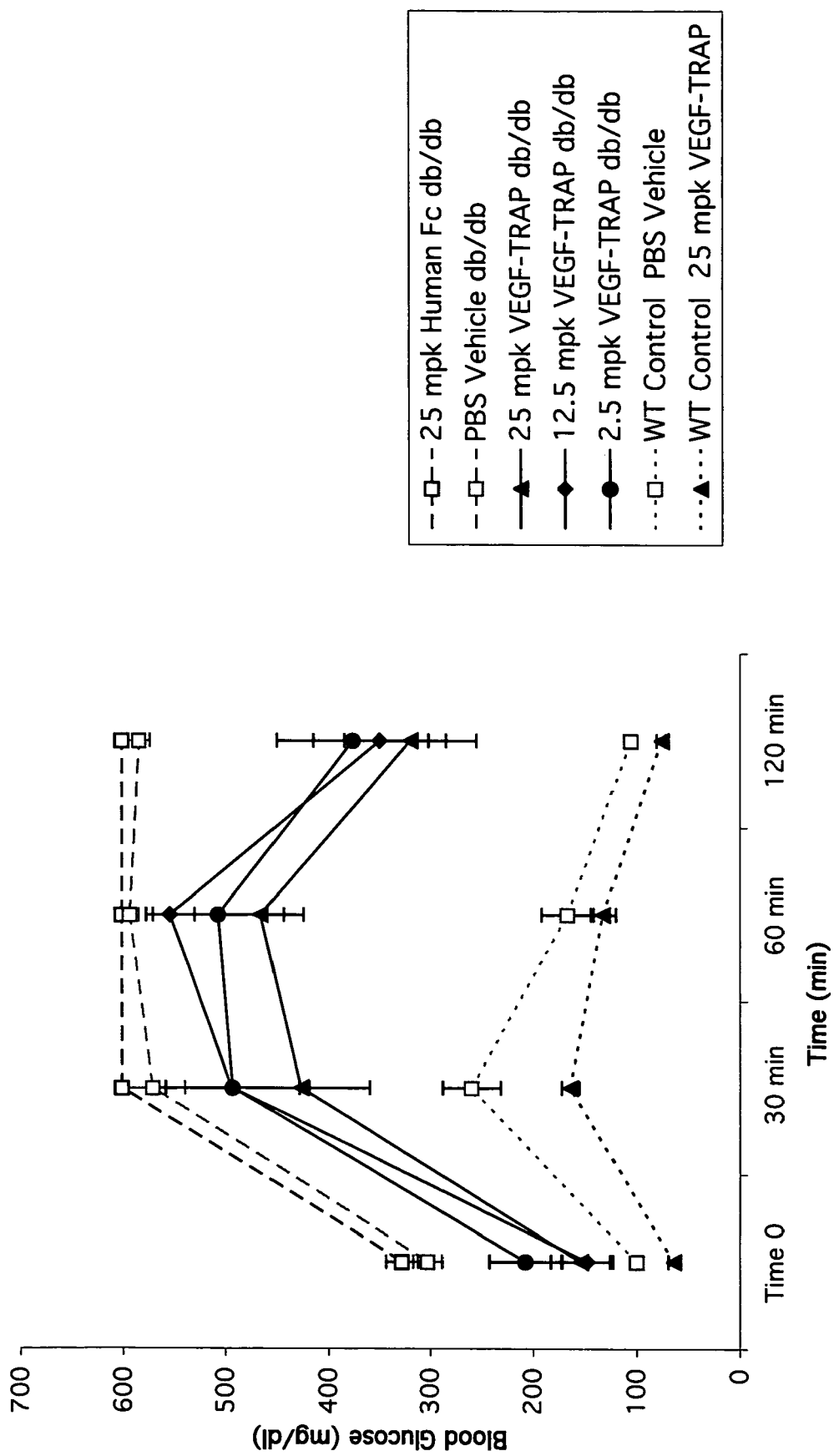

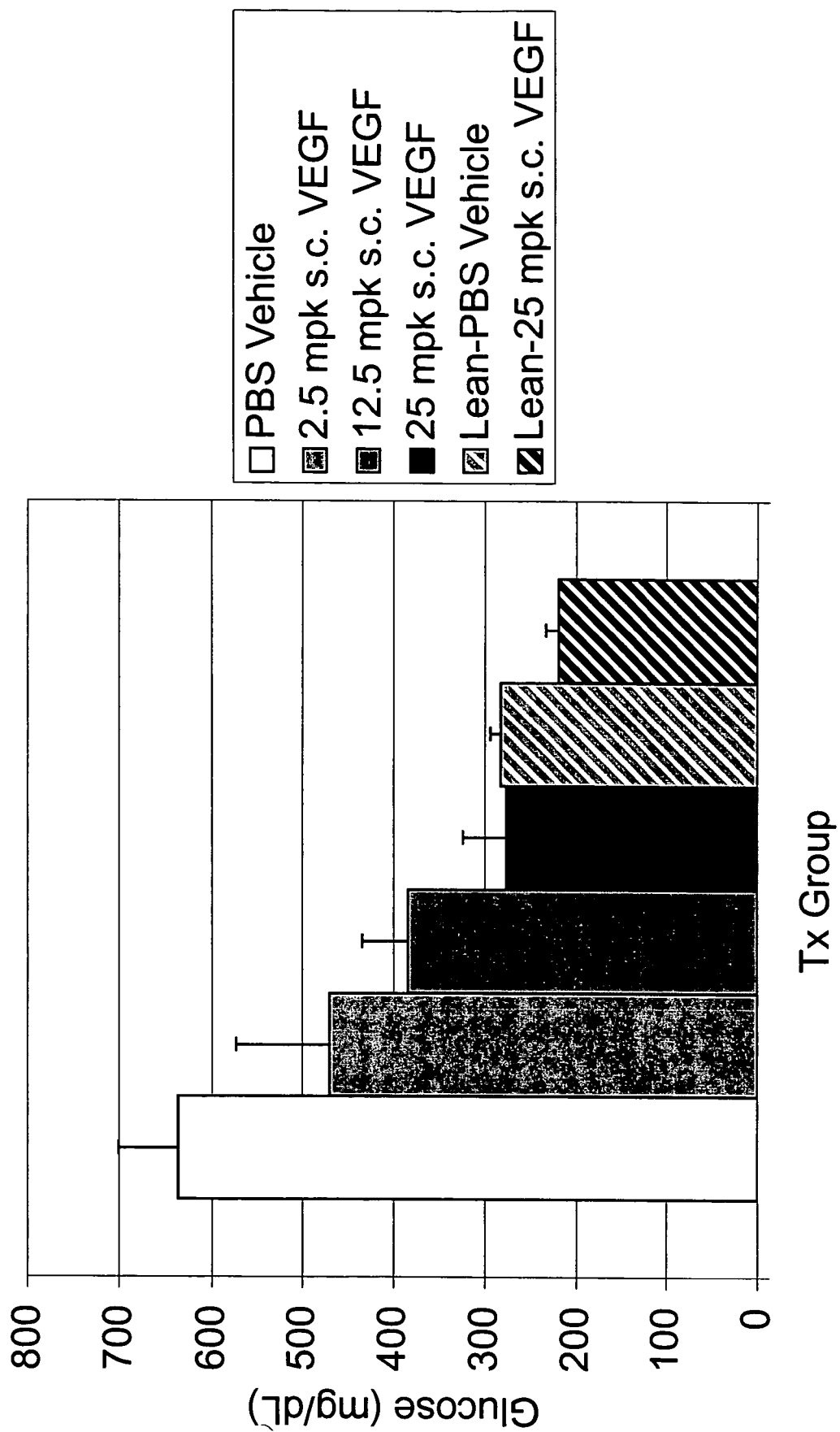

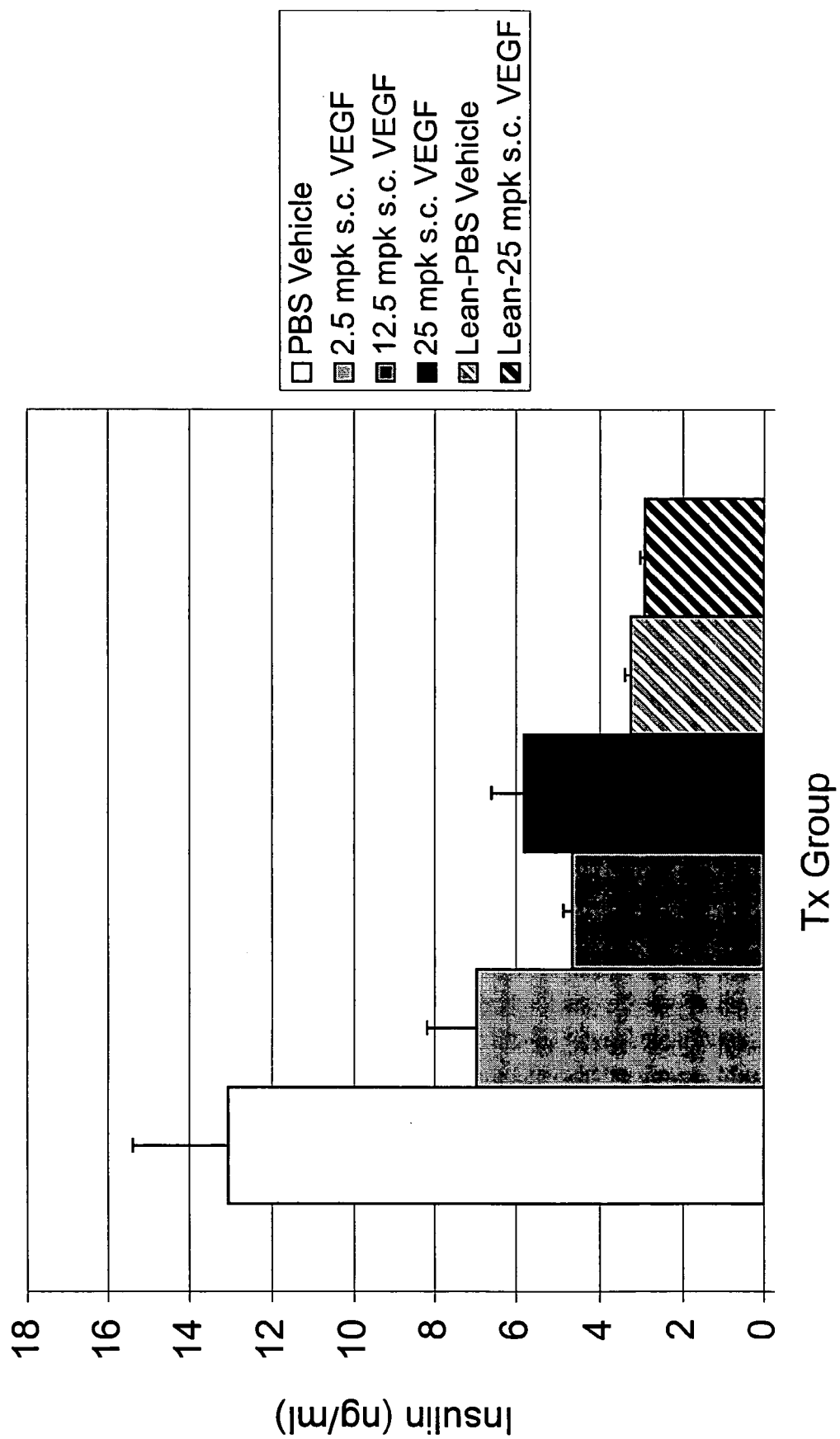

SEQUENCE LISTING

```
<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1
atggtcagct actgggacac cggggtcctg ctgtgcgcgc tgctcagctg tctgcttctc        60
acaggatcta gttccggaag tgataccggt agacctttcg tagagatgta cagtgaaatc       120
cccgaaatta tacacatgac tgaaggaagg gagctcgtca ttccctgccg ggttacgtca       180
cctaacatca ctgttacttt aaaaaagttt ccacttgaca cttttgatccc tgatggaaaa      240 cgcataatct gggacagtag aaagggcttc atcatatcaa atgcaacgta caaagaaata      300
gggcttctga cctgtgaagc aacagtcaat gggcatttgt ataagacaaa ctatctcaca       360
catcgacaaa ccaatacaat catagatgtg gttctgagtc cgtctcatgg aattgaacta       420
tctgttggag aaaagcttgt cttaaattgt acagcaagaa ctgaactaaa tgtggggatt      480
gacttcaact gggaatacccc ttcttcgaag catcagcata agaaacttgt aaaccgagac       540
ctaaaaaccc agtctgggag tgagatgaag aaattttttga gcaccttaac tatagatggt       600
```

```
gtaacccgga gtgaccaagg attgtacacc tgtgcagcat ccagtgggct gatgaccaag      660
aagaacagca catttgtcag ggtccatgaa aaggacaaaa ctcacacatg cccaccgtgc      720
ccagcacctg aactcctggg gggaccgtca gtcttcctct ccccccaaa acccaaggac       780 accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca   1020 gccccatcg agaaaaccat ctccaaagcc aagggcagc cccgagaacc acaggtgtac    1080
accctgcccc catcccggga tgagctgacc aagaaccagg tcagcctgac ctgcctggtc   1140
aaaggcttct atcccagcga catcgccgtg gagtgggaga gcaatgggca gccggagaac  1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga     1377
```

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
             20                  25                  30

Phe Val Glu Met Tyr Ser Glu Ile Pro Glu Ile Ile His Met Thr Glu
         35                  40                  45

Gly Arg Glu Leu Val Ile Pro Cys Arg Val Thr Ser Pro Asn Ile Thr
     50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240
```

-continued

```
Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
450                 455
```

METHODS OF TREATING DIABETES BY BLOCKING VEGF-MEDIATED ACTIVITY

CROSS-REFERENCE TO RELATED APPLICATIONS

This application claims the benefit under 35 USC § 119(e) of U.S. Provisional 60/458,790 filed 28 Mar. 2003, which application is herein specifically incorporated by reference in its entirety.

BACKGROUND

1. Field of the Invention

The field of the invention is generally related to methods of treating diabetes by administering agents capable of decreasing serum glucose levels. In particular, the field of the invention is methods of treating diabetes by administering agents capable of blocking, inhibiting, or ameliorating VEGF-mediated activity.

2. Description of Related Art

It has been reported that db/db mice, a murine model of type 2 diabetes, treated with an antibody against VEGF show amelioration of diabetic renal changes, but do not exhibit a decrease in body weight, serum glucose levels, insulin levels or food consumption (Flyvbjerg et al. (2002) Diabetes 51:3090–3094).

BRIEF SUMMARY OF THE INVENTION

In a first aspect, the invention features a method of treating diabetes comprising administering to a mammal an agent capable of blocking, inhibiting, or ameliorating VEGF-mediated activity. In specific embodiments, the method of treatment of the invention results in decreased serum glucose levels, improved glucose tolerance, improved insulin sensitivity, reduced hyperinsulinemia, and/or improved glycemic control.

In a specific embodiment, the diabetes treated is Type 2 diabetes (also termed non-insulin dependent diabetes mellitus) (NIDDM). In specific conditions, Type I diabetes or gestational diabetes may also be treated.

The agent capable of blocking, inhibiting, or ameliorating VEGF-mediated activity in specific embodiments is a VEGF antagonist. More specifically, the VEGF antagonist includes a VEGF trap selected from the group consisting of acetylated Flt-1(1-3)-Fc, Flt-1(1-3$_{R->N}$)-Fc, Flt-1(1-3$_{AB}$)-Fc, Flt-1(2-3$_{AB}$)-Fc, Flt-1(2-3)-Fc, Flt-1D2-VEGFR3D3-FcΔC1(a), Flt-1D2-Flk-1D3-FcΔC1(a), and VEGFR1R2-FcΔC1(a). In other specific embodiments, the agent is an antibody, lipid, nucleic acid, small molecule, aptamer, antisense molecule, carbohydrate, peptidomimetic, or hapten.

Administration of the agent may be by any method known in the art, including subcutaneous, intramuscular, intradermal, intraperitoneal, intravenous, intranasal, or oral routes of administration.

The mammal treated is preferably a human subject suffering from diabetes. Also suitable for treatment by the method of the invention is a subject at risk for development of type 2 diabetes who exhibits one or more symptoms of type 2 diabetes or of a condition associated with the development of type 2 diabetes, such as, for example, such as insulin resistance, dyslipidemia, polycystic ovarian syndrome, obesity, hyperglycemia, hyperlipidemia, hypercholesteremia, hypertriglyceridemia, hyperinsulinemia, and hypertension.

In a second aspect, the invention features a method of inhibiting or slowing the progression of type 2 diabetes in a mammal, comprising administering to a mammal an agent capable of blocking or inhibiting VEGF-mediated activity.

In a third aspect, the invention features a method of improving glucose tolerance or insulin sensitivity in a mammal in need thereof, comprising administering to a mammal an agent capable of blocking or inhibiting VEGF-mediated activity.

Other objects and advantages will become apparent from a review of the ensuing detailed description.

BRIEF DESCRIPTION OF THE FIGURES

FIGS. 1A–B: (A) Serum glucose levels and (B) body weight at 4 weeks in diabetic (db/db) and non-diabetic (db/?) mice treated with VEGFR1R2-FcΔC1(a).

FIG. 2: Serum glucose levels through 8 weeks of treatment of controls and treated diabetic (db/db) and non-diabetic (db/?) mice with VEGFR1R2-FcΔC1(a).

FIG. 3: Oral glucose tolerance test at 4 weeks of treatment for control and VEGFR1R2-FcΔC1(a)-treated diabetic (db/db) mice and non-diabetic (db/?) mice.

FIG. 4: Oral glucose tolerance test at 8 weeks of treatment for control and VEGFR1R2-FcΔC1(a)-treated diabetic (db/db) mice and non-diabetic (db/?) mice.

FIG. 5A–B Fasting serum glucose and insulin levels after 8 weeks of treatment of control and VEGFR1R2-FcΔC1(a)-treated diabetic (db/db) mice and non-diabetic (db/?) mice.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

The invention is based in part on the finding that administration of an agent capable of blocking or inhibiting VEGF-mediated activity is capable of decreasing serum glucose and improving glucose disposal in diabetic mammals. These findings represent the first time an agent capable of blocking or inhibiting VEGF-mediated activity has been shown to ameliorate diabetes. Thus, the invention provides for methods of treating diabetes in a mammal by administering a VEGF antagonist. More specifically, the method of the invention may be practiced with a VEGF antagonist such as a VEGF trap, as shown below, or a VEGF-specific antibody.

Definitions

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of a VEGF blocker or inhibitor is a VEGF receptor-based antagonist including, for example, an anti-VEGF antibody, or a VEGF trap such as VEGFR1R2-FcΔC1(a) (SEQ ID NOs:1–2). For a complete description of VEGF-receptor based antagonists including VEGFR1R2-FcΔC1(a), see PCT publication WO/00/75319, the contents of which is incorporated in its entirety herein by reference.

A "small molecule" is defined herein to have a molecular weight below about 500 Daltons, and may include chemical as well as peptide molecules.

Nucleic Acid Constructs

Individual components of the VEGF-specific fusion proteins of the invention may be constructed by molecular biological methods known to the art with the instructions provided by the instant specification. These components are selected from a first cellular receptor protein, such as, for example, VEGFR1; a second cellular receptor protein, such as, for example, VEGFR2; a multimerizing component, such as an Fc.

Specific embodiments of the VEGF-specific fusion proteins useful in the methods of the invention comprise a multimerizing component which allows the fusion proteins to associate, e.g., as multimers, preferably dimers. Preferably, the multimerizing component comprises an immunoglobulin derived domain. Suitable multimerizing components are sequences encoding an immunoglobulin heavy chain hinge region (Takahashi et al. 1982 Cell 29:671–679); immunoglobulin gene sequences, and portions thereof.

The nucleic acid constructs encoding the fusion proteins useful in the methods of the invention are inserted into an expression vector by methods known to the art, wherein the nucleic acid molecule is operatively linked to an expression control sequence. Host-vector systems for the production of proteins comprising an expression vector introduced into a host cell suitable for expression of the protein are known in the art. The suitable host cell may be a bacterial cell such as *E. coli*, a yeast cell, such as *Pichia pastoris,* an insect cell, such as *Spodoptera frugiperda,* or a mammalian cell, such as a COS, CHO, 293, BHK or NS0 cell.

Antisense Nucleic Acids

In one aspect of the invention, VEGF-mediated activity is blocked or inhibited by the use of VEGF antisense nucleic acids. The present invention provides the therapeutic or prophylactic use of nucleic acids comprising at least six nucleotides that are antisense to a gene or cDNA encoding VEGF or a portion thereof. As used herein, a VEGF "antisense" nucleic acid refers to a nucleic acid capable of hybridizing by virtue of some sequence complementarity to a portion of an RNA (preferably mRNA) encoding VEGF. The antisense nucleic acid may be complementary to a coding and/or noncoding region of an mRNA encoding VEGF. Such antisense nucleic acids have utility as compounds that prevent VEGF expression, and can be used in the treatment of diabetes. The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The VEGF antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. In addition, the antisense molecules may be polymers that are nucleic acid mimics, such as PNA, morpholino oligos, and LNA. Other types of antisence molecules include short double-stranded RNAs, known as siRNAs, and short hairpin RNAs, and long dsRNA (>50 bp but usually ≧500 bp).

Inhibitory Ribozymes

In aspect of the invention, diabetes may be treated in a subject suffering from such disease by decreasing the level of VEGF activity by using ribozyme molecules designed to catalytically cleave gene mRNA transcripts encoding VEGF, preventing translation of target gene mRNA and, therefore, expression of the gene product.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246. While ribozymes that cleave mRNA at site-specific recognition sequences can be used to destroy mRNAs encoding VEGF, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art. The ribozymes of the present invention also include RNA endoribonucleases (hereinafter "Cech-type ribozymes") such as the one that occurs naturally in *Tetrahymena thermophila* (known as the IVS, or L-19 IVS RNA). The Cech-type ribozymes have an eight base pair active site that hybridizes to a target RNA sequence where after cleavage of the target RNA takes place. The invention encompasses those Cech-type ribozymes that target eight base-pair active site sequences that are present in the gene encoding VEGF.

Generation of Antibodies to VEGF Proteins

In another aspect of the invention, the invention may be practiced with an anti-VEGF antibody or antibody fragment capable of binding and blocking VEGF activity. Anti-VEGF antibodies are disclosed, for example, in U.S. Pat. No. 6,121,230, herein specifically incorporated by reference. The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. $IgG_1$, $IgG_2$, etc.). Typically, the antigen-binding region of an antibody will be the most critical in determining specificity and affinity of binding.

Antibodies exist as intact immunoglobulins, or as a number of well-characterized fragments produced by digestion with various peptidases. For example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms antibody, as used herein, also includes antibody fragments either produced by the modification of whole antibodies, or those synthesized de novo using recombinant DNA methodologies (e.g., single chain Fv)(scFv) or those identified using phage display libraries (see, for example, McCafferty et al. (1990) Nature 348:552–554).

Methods for preparing antibodies are known to the art. See, for example, Kohler & Milstein (1975) Nature 256: 495–497; Harlow & Lane (1988) *Antibodies: a Laboratory Manual*, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. No. 4,946,778; U.S. Pat. No. 4,816,567) can be adapted to produce antibodies used in the fusion proteins and methods of the instant invention. Also, transgenic mice, or other organisms such as other mammals, may be used to express human or humanized antibodies. Alternatively, phage display technology can be used to identify antibodies and heteromeric Fab fragments that specifically bind to selected antigens.

Antibody Screening and Selection

Screening and selection of preferred antibodies can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of the multi-specific fusion proteins of the invention. Secondary screening may be conducted with any suitable method known to the art. One preferred method, termed "Biosensor Modification-Assisted Profiling" ("BiaMAP") is described in co-pending U.S. Ser. No. 60/423,017 filed 01 November 2002, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody:antigen interactions.

Treatment Population

The number of people suffering with diabetes mellitus is expected to reach 300 million by the year 2009 (*Type 2 Diabetes Prediction and Prevention* (1999) ed. G. A. Hitman, John Wiley & Sons), of which about 80–90% are type 2 diabetes. Diabetic retinopathy is a leading cause of blindness; other complications of diabetes include renal disease, foot problems and neuropathic conditions. In type 1 or insulin dependent diabetes mellitus (IDDM) the insulin-producing B cells of the pancreas are destroyed by what is probably an autoimmune disease. Insulin replacement is the preferred therapy.

The pathogenesis of type 2 or non insulin dependent diabetes mellitus (NIDDM) has though been determined to result from both a B cell defect and insulin resistance. Thus, patients with type 2 NIDDM have the two physiological defects of hypersecretion of insulin (during the early phase of type 2 diabetes) and resistance to insulin in target tissues. Thus, in the first phase of NIDDM, the plasma glucose level is normal despite demonstrable insulin-resistance with elevated insulin levels. In the second phase insulin resistance worsens so that postprandial hyperglycemia develops despite elevated insulin. In the third or late phase of type 2 diabetes, insulin resistance does not change but declining insulin secretion causes fasting hyperglycemia and overt diabetes.

Disorders associated with insulin resistance include NIDDM, diabetic angiopathy, atherosclerosis, diabetic nephropathy, diabetic neuropathy, and diabetic ocular complications such as retinopathy, cataract formation and glaucoma, as well as glucocorticoid induced insulin resistance, dyslipidemia, polycysitic ovarian syndrome, obesity, hyperglycemia, hyperlipidemia, hypercholesterolemia, hypertriglyceridemia, hyperinsulinemia, and hypertension.

Accordingly, the population to be treated by the method of the invention are subjects suffering from NIDDM, subjects suffering from insulin resistance, and subjects at risk for worsening of NIDDM or insulin resistance. Further, a subject with one or more symptoms associated with NIDDM is a candidate for treatment by the method of the invention. The diagnosis of a patient at risk for development of NIDDM or suffering from NIDDM is preferably made by a qualified clinician. Methods for diagnosing NIDDM are described, for example, in U.S. Pat. No. 5,719,022, herein specifically incorporated by reference.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents.

In another embodiment, the active agent can be delivered in a vesicle, in particular a liposome (see Langer (1990) Science 249:1527–1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

Cellular Transfection and Gene Therapy

The present invention encompasses the use of nucleic acids encoding the VEGF-specific fusion proteins of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. Reintroduction of transfected cells may be accomplished by any method known to the art, including re-implantation of encapsulated cells. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of treating diabetes in a human comprising transfecting a cell with a nucleic acid encoding a VEGF-specific fusion protein of the invention, wherein the nucleic acid comprises an inducible promoter operably linked to the nucleic acid encoding the VEGF-specific fusion protein. For gene therapy procedures in the treatment or prevention of human disease, see for example, Van Brunt (1998) Biotechnology 6:1149–1154.

Combination Therapies

In numerous embodiments, the VEGF-specific fusion proteins of the present invention may be administered in combination with one or more additional compounds or therapies. Combination therapy includes administration of a single pharmaceutical dosage formulation which contains a VEGF-specific fusion protein and one or more additional hypoglycemic agent or weight loss agent; as well as administration of a VEGF-specific fusion protein and one or more additional hypoglycemic-agent or weight loss agent in its own separate pharmaceutical dosage formulation. For example, a VEGF-specific fusion protein of the invention and a hypoglycemic agent can be administered to the patient together in a single oral dosage composition such as a tablet or capsule, or each agent administered in separate oral dosage formulations. Where separate dosage formulations are used, the VEGF-specific fusion protein of the invention and one or more additional hypoglycemic agents can be administered at essentially the same time, i.e., concurrently, or at separately staggered times, i.e., sequentially.

An examples of such weight loss agents is Axokine® (Regeneron) (a genetically engineered version of human ciliary neurotrophic factor (CNTF). Examples of such hypoglycemic agents include: insulin; biguanidines such as metformin (the generic name for Glucophage® (BMS)) an oral formulation to lower blood glucose by keeping the liver from releasing too much glucose, and buformin; sulfonylureas such as acetohexamide, Diabinese® (Pfizer) (generic name chloropropamide), an oral antidiabetic medication to treat Type II diabetes, Amaryl® (Aventis) (generic name "Glimepiride"), an oral formulation to correct insulin deficiency by producing insulin, Glynase Pres Tabs® (Pharmacia) (generic name "Glyburide"), an oral formulation to lower blood glucose, Glucotrol XL® (Roering Pfizer) (generic name "Glipidize" extended release), an oral formulation to lower blood glucose, tolazamide, tolbutamide, DiaBeta® (Hoechst) (generic name "Glyburide"), Glucotrol® (Pfizer) (generic name "Glipidize") and glyclazide; thiazolidinediones, such as Rezulin® (Park Davis) (generic name "Troglitazone"), an anti-hyperglycemic drug that increases insulin sensitivity in skeletal muscle and decreases glucose production in the liver, Actos® (Tekada) (generic name "Pioglitazone"), an oral formulation to improve insulin action), and Avandia® (GSK) (generic name "Rosiglitazone"), an oral formulation that improves insulin action); α-glycosidase inhibitors, such as Precose® (Bayer) (generic name "Acarbose"), an oral formulation to lower blood glucose by slowing carbohydrate digestion and Glyset® (Bayer) (generic name "Miglitol"), an oral formulation to lower blood glucose by slowing carbohydrate digestion; Meglitinide such as Prandin® (Novo Nordisk) (generic name "Repaglinide"), an oral formulation taken prior to meals and rapidly absorbed to stimulate the pancreas to produce insulin; glucose elevating agents such as Glucagon® (Lilly) (generic name "Glipidize"), an oral formulation to lower blood glucose; and $\beta_3$ adrenoreceptor agonists such as CL-316,243.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment of diabetes can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 50–5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

The invention also provides an article of manufacturing comprising packaging material and a pharmaceutical agent contained within the packaging material, wherein the pharmaceutical agent comprises at least one VEGF-specific fusion protein of the invention and wherein the packaging material comprises a label or package insert which indicates that the VEGF-specific fusion protein can be used for treating diabetes.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of VEGFR1R2-FcΔC1(a) Treatment in Diabetic (db/db) Mice

Diabetic (db/db) mice at 8–10 weeks of age were acclimated for 1 week and treatment began after this point. Groups of db/db mice (n=6) were randomly assigned by weight and treated by s.c. injection once a week for 4 weeks with one of the following compositions: carrier (Vehicle); FcΔC1 protein (Fc); or 25, 12.5, or 2.5 mg/kg of VEGFR1R2-FcΔC1(a). Additionally, two groups of non-diabetic (db/?) mice were treated by s.c. injection as follows: 25 mg/kg of VEGFR1R2-FcΔC1(a) and carrier (Diabetic Vehicle). Blood glucose levels were assessed at the same time each week immediately before the next injection for the 4 weeks of treatment. All groups were assessed at this time by an oral glucose tolerance test. Treatment of animals was continued for a further 4 weeks (8 weeks total) following the regimen described above, and blood glucose levels were assessed after 8 weeks of treatment.

Results at 4 weeks of treatment. All diabetic (db/db) animals had developed hyperglycemia at the staring time of the experiment as shown by the elevated blood glucose (Preface DIA—groups in FIG. 1A at time 0). Animals treated with 25, 12.5 and 2.5 mg/kg VEGFR1R2-FcΔC1(a) showed a significant and progressive reduction in serum glucose over the 8 week treatment period. Animals treated with 25, 12.5 and 2.5 mg/kg VEGFR1R2-FcΔC1(a) did not show a significant reduction in body weight compared to Vehicle or FcΔC1 control mice over the first 4 week period (repeated measures ANOVA, N.S. see FIG. 1B).

Results for 8 Weeks of treatment. All diabetic (db/db) animals still exhibited hyperglycemia as shown by the elevated blood glucose (Preface DIA-groups in FIG. 2 at time week 8). Animals treated with 25, 12.5 and 2.5 mg/kg VEGFR1R2-FcΔC1(a) showed a significant reduction in serum non fasted blood glucose over the 8 week treatment period (repeated measures ANOVA, d.f. 4, 25, $F_{Group}$=6.36 p=0.001, $F_{Time}$=38.5 p<0.0001; $F_{interaction}$=1.8 p=0.04; see FIG. 1A).

Example 2

Effect of VEGFR1R2-FcΔC1(a) on Oral Glucose Tolerance in Diabetic Mice

Diabetic (db/db) and non-diabetic (db/?) mice mice at 8–10 weeks of age were treated as described above.

The ability to dispose of a bolus of glucose delivered into the stomach by gavage was assessed after 4 injections (week 5) and after 8 injections (at week 9). For this assessment, mice are deprived of food for approximately 18 hours and after being gavaged, blood glucose was measured at 0, 30, 60 and 120 min.

Results for 4 weeks of treatment. Vehicle and FcΔC1 protein treated diabetic (db/db) mice had an impaired ability to dispose of glucose compared to lean non-diabetic (db/?) control mice (FIG. 3). After 4 injections (in the $5^{th}$ week) animals treated with 25, 12.5 and 2.5 mg/kg VEGFR1R2-FcΔC1(a) showed a significant improvement in the ability to dispose of the administered glucose. These results demonstrate that VEGF inhibition improves glucose tolerance in diabetic mammals. In contrast, the Vehicle and FcΔC1 protein treated diabetic (db/db) mice show no improvement in the ability to dispose of glucose or glucose tolerance (FIG. 3).

Results for 8 weeks of treatment. Vehicle and FcΔC1 protein treated diabetic (db/db) mice still had an impaired ability to dispose of glucose compared to lean non-diabetic (db/?) control mice (FIG. 4). After a total of 8 injections (in the $9^{th}$ week) animals treated with 25, 12.5 and 2.5 mg/kg VEGFR1R2-FcΔC1(a) showed a significant improvement in the ability to dispose of the administered glucose. These results demonstrate that VEGF inhibition improves glucose tolerance in diabetic mammals. In contrast, the Vehicle and FcΔC1 protein treated diabetic (db/db) mice show no improvement in the ability to dispose of glucose or glucose tolerance (FIG. 4).

Example 3

Effect of VEGFR1R2-FcΔC1(a) Treatment on Fasting Serum Glucose and Insulin in Diabetic (db/db) Mice Diabetic (db/db) mice were acclimated for 1 week and treatment began as described above. After 8 injections (in the $9^{th}$ week) fasting blood glucose and insulin (FIG. 5B) was assessed.

Vehicle and FcΔC1 protein treated diabetic (db/db) mice had elevated fasting blood glucose levels compared to lean non diabetic (db/?) control mice (FIG. 5A). VEGFR1R2-FcΔC1(a)-treated animals showed a significant reduction in fasting serum glucose compared to diabetic controls (Vehicle or FcCΔ1; FIG. 5A) and a significantly reduced insulin level. This demonstrates that VEGF inhibition improves not only hyperglycemia in a diabetic mammal but also improves insulin sensitivity.

The present invention may be embodied in other specific forms without departing from the spirit or essential attributes thereof.

We claim:

1. A method of treating non-insulin dependent diabetes mellitus (NIDDM) in a mammal, comprising administering to the mammal a VEGF antagonist such that diabetes is treated, and wherein the VEGF antagonist is VEGFR1R2-FcΔC1(a).

2. The method of claim 1 wherein the treatment of diabetes results in one or more of decreased serum glucose concentrations, improved glucose tolerance, increased insulin sensitivity, and reduced hyperinsulinemia.

3. A method of improving glucose tolerance or insulin sensitivity in a human subject in need thereof, comprising administering to the subject a VEGF antagonist such that glucose tolerance or insulin sensitivity is improved, and wherein the VEGF antagonist is VEGFR1R2-FcΔC1(a).

4. The method of claim 1, wherein VEGFR1R2-FcΔc1(a) comprises the amino acid sequence of SEQ ID NO:2.

5. The method of claim 4, wherein VEGFR1R2-FcΔc1(a) is encoded by the nucleic acid sequence of SEQ ID NO:1.

6. The method of claim 3, wherein VEGFR1R2-FcΔc1(a) comprises the amino acid sequence of SEQ ID NO:2.

7. The method of claim 6, wherein VEGFR1R2-FcΔc1(a) is encoded by the nucleic acid sequence of SEQ ID NO:1.

8. The method of claim 1, wherein the administering is by injection.

9. The method as claimed in claim 8, wherein the injection is subcutaneous injection.

10. The method as claimed in claim 8, wherein the injection is intravenous injection.

11. The method of claim 3, wherein the administering is by injection.

12. The method as claimed in claim 11, wherein the injection is subcutaneous injection.

13. The method as claimed in claim 11, wherein the injection is intravenous injection.

* * * * *